:::
United States Patent [19]

Barsky

[11] Patent Number: 5,649,896

[45] Date of Patent: Jul. 22, 1997

[54] DRAFT SHIELD FOR INFANT RADIANT WARMER

[75] Inventor: Barry E. Barsky, Huntingdon Valley, Pa.

[73] Assignee: Air-Shields, Inc., Hatboro, Pa.

[21] Appl. No.: 527,926

[22] Filed: Sep. 14, 1995

Related U.S. Application Data

[62] Division of Ser. No. 303,413, Sep. 9, 1994, Pat. No. 5,498,229.

[51] Int. Cl.$^6$ .............................. A61G 11/00; H05B 3/34
[52] U.S. Cl. ................................................ 600/22
[58] Field of Search .................. 600/22; 219/385, 219/526, 527, 543, 203, 411, 405

[56] References Cited

U.S. PATENT DOCUMENTS

| | | |
|---|---|---|
| 2,365,243 | 12/1944 | Boren . |
| 2,409,083 | 10/1946 | Valverde . |
| 3,858,570 | 1/1975 | Beld et al. . |
| 3,878,361 | 4/1975 | Levin et al. . |
| 3,898,427 | 8/1975 | Levin et al. ........................ 600/22 |
| 4,121,571 | 10/1978 | Pickering . |
| 4,809,677 | 3/1989 | Mackin et al. . |
| 4,936,824 | 6/1990 | Koch et al. . |
| 5,119,467 | 6/1992 | Barsky et al. . |
| 5,471,036 | 11/1995 | Sperbeck ........................ 219/543 |

FOREIGN PATENT DOCUMENTS

| | | |
|---|---|---|
| 0 291 280 A1 | 11/1988 | European Pat. Off. . |
| 0 308 093 A3 | 3/1989 | European Pat. Off. . |

*Primary Examiner*—Lee S. Cohen
*Assistant Examiner*—Samuel Gilbert
*Attorney, Agent, or Firm*—Ratner & Prestia

[57] ABSTRACT

A infant radiant warmer having a bassinet assembly which includes a plurality of optically transparent electrothermal side panels surrounding a mattress assembly upon which a infant can be placed. The side panels serve both as radiant shields which reduce radiant heat losses from the infant and as sources of radiant heat which add to the warmth provided by an overhead infrared heater to the infant. This infant radiant warmer also has an optically transparent draft shield assembly which serves to maintain the environment of the bassinet assembly by inhibiting the effects of drafts, air-conditioning and disruptive temperatures in the atmosphere outside the bassinet assembly. Preferably, a humidifier is provided for humidifying the atmosphere within which the infant is placed.

2 Claims, 5 Drawing Sheets

:::

1

DRAFT SHIELD FOR INFANT RADIANT WARMER

This application is a division of application Ser. No. 08/303,413, filed Sep. 09, 1994, U.S. Pat. No. 5,498,229.

TECHNICAL FIELD

The present invention relates, in general, to the treatment of infants and, in particular, to an infant radiant warmer used in maintaining an infant in a prescribed controlled environment.

BACKGROUND OF THE INVENTION

At the present time, there are many infant warmers in use for the treatment and maintenance of ultra-low-birth-weight babies (i.e. infants of extremely low birth weight). Such infant warmers typically include an overhead infrared heater which is the source of warmth for an infant placed in the warmer and having the major portion of its body exposed for clinical purposes. So exposed, the infant can suffer insensible water loss during prescribed therapy which is caused by exposure of the infant to the infrared heater.

It is common practice for the clinician to place a thin-sheet plastic material over the exposed surfaces of the infant to minimize insensible water loss. This material is PVC which has a relatively high plasticizer content introduced in the formulation of the PVC material. The plasticizer causes the PVC material to adhere to itself and other materials or surfaces such as human skin.

As such, the PVC material, while inhibiting insensible water loss, can tear or disassociate regions of the skin of the infant to which it has adhered. It is known that infants which require treatment in an infant warmer have regions of embryonic dermal membrane which can be displaced relatively easily. Thus, use of thin-sheet PVC material, while solving one problem, can be the source of another problem. In addition, because of the adhesive nature of PVC material, microbiological organisms can adhere to the surfaces of the thin-sheet PVC material or grow on these surfaces.

SUMMARY OF THE INVENTION

Accordingly, an infant radiant warmer, constructed in accordance with the present invention, includes a base and a bassinet assembly supported by the base and including (a) a mattress assembly upon which an infant can be placed, (b) a plurality of vertically disposed optically transparent electrothermal side panels surrounding the mattress assembly, and (c) an optically transparent draft shield assembly disposed over the mattress assembly and movable between a completely closed position and a completely open position. Also included in this infant radiant warmer is an overhead infrared heater supported by the base and disposed above the bassinet assembly to radiate heat through the optically transparent draft shield assembly to an infant placed on the mattress assembly.

Another aspect of the present invention is the particular construction of the two optically transparent draft shield assemblies which are disclosed. While each is especially useful in an infant radiant warmer constructed in accordance with the present invention, each has potential utility in or with other apparatus.

Yet another aspect of the present invention is the particular construction of humidifying apparatus which can be included in an infant radiant warmer constructed in accordance with the present invention. This humidifying apparatus also has potential utility in or with other apparatus.

DETAILED DESCRIPTION OF THE INVENTION

Figure 1:
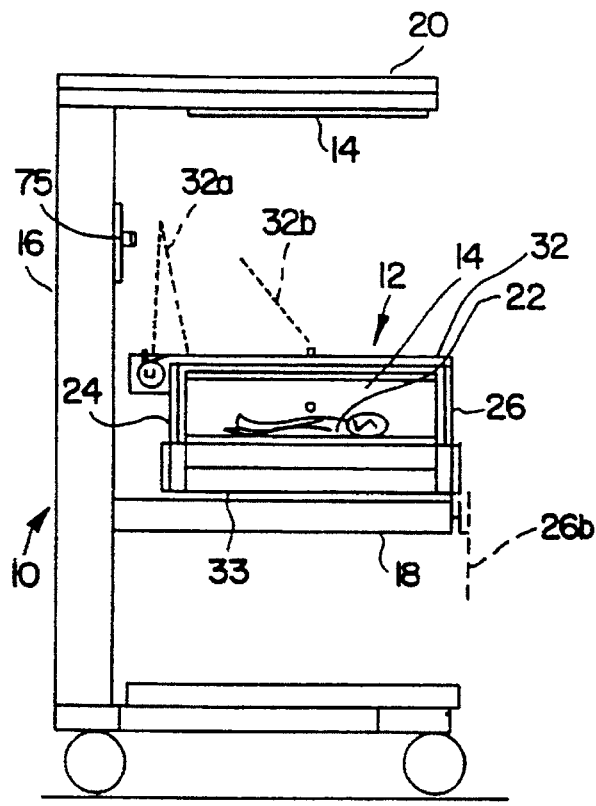
FIG. 1 is a side view of a preferred embodiment of an infant radiant warmer constructed in accordance with the present invention.

Referring to FIG. 1, an infant radiant warmer, constructed in accordance with the present invention, includes a base 10, a bassinet assembly 12 supported by the base, and an overhead infrared heater 14 also supported by the base. Overhead infrared heater 14 is disposed above bassinet assembly 12 to radiate heat to an infant placed within the bassinet assembly.

For the embodiment of the invention illustrated in FIG. 1, base 10 includes a vertical post 16, a horizontal pedestal 18 extending from the vertical post, and a horizontal overhang member 20 also extending from the vertical post. Bassinet assembly 12 is supported on horizontal pedestal 18 and overhead infrared heater 14 is supported from horizontal overhang member 20.

Figure 4:
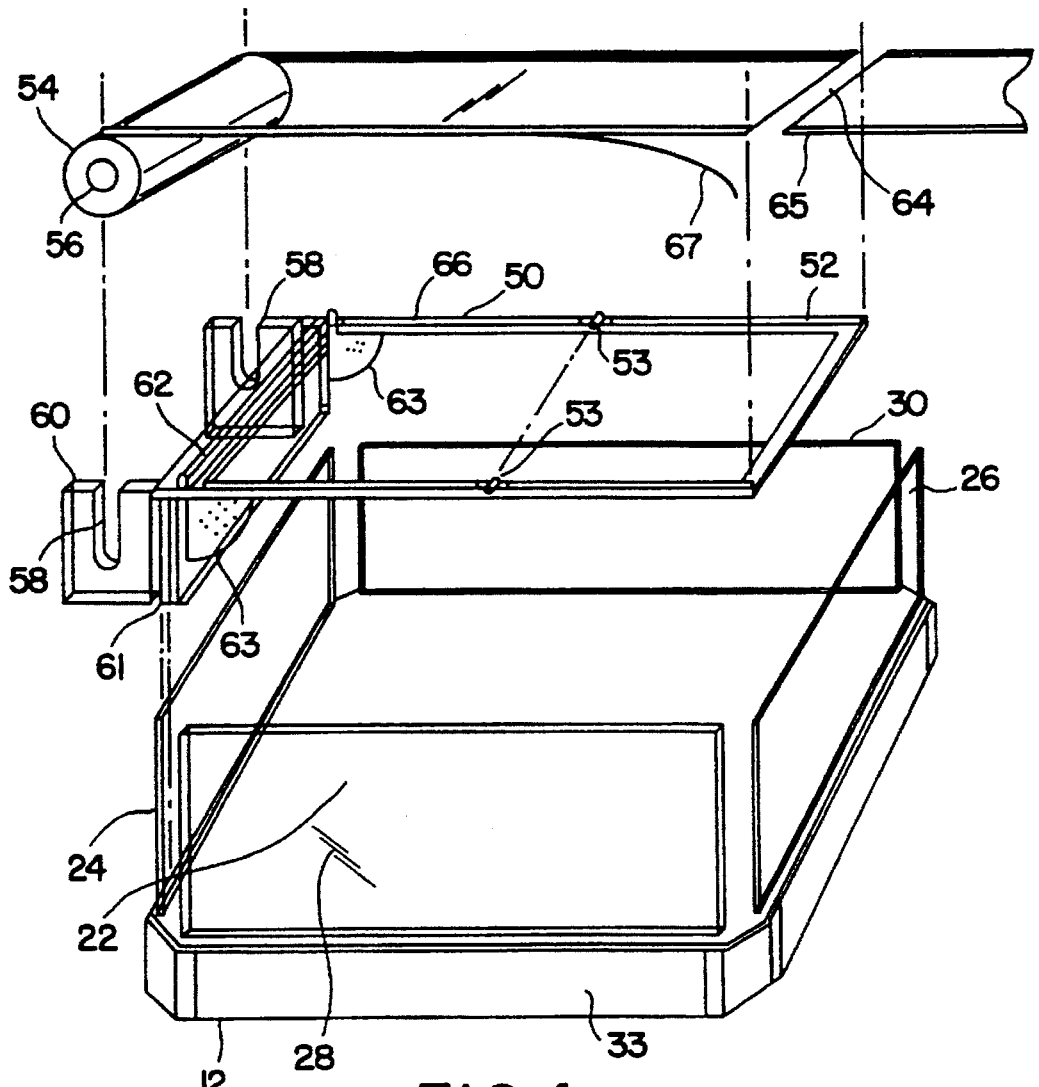
FIG. 4 is an exploded perspective view of a first preferred embodiment of an optically transparent draft shield assembly constructed in accordance with the present invention and included in an infant radiant warmer constructed in accordance with the present invention.

Bassinet assembly 12 includes a mattress assembly 22 upon which an infant can be placed. As shown in FIG. 4, mattress assembly 22 is surrounded by a plurality of vertically disposed optically transparent electrothermal side panels 24, 26, 28 and 30 which reduce radiant heat losses from the infant and contribute to providing warmth to the infant. Preferably, optically transparent electrothermal side panels 26, 28 and 30 are mounted to swing outwardly permitting access to an infant on the mattress assembly. In FIG. 1, the open position of optically transparent electrothermal side panel 26 is represented by the dashed lines identified by reference numeral 26b.

Bassinet assembly 12 also includes an optically transparent draft shield assembly 32 which is disposed over mattress assembly 22 and is supported from optically transparent electrothermal side panel 24 as described below. Optically transparent draft shield assembly 32 serves to maintain the environment of bassinet assembly 12 by inhibiting the effects of drafts, air-conditioning and disruptive temperatures in the atmosphere outside the bassinet assembly. Optically transparent draft shield assembly 32 is movable between a completely closed position and a completely open position, the latter being represented by the dashed lines in FIG. 1 which are identified by reference numeral 32a. Reference numeral 32b represents a partially open position of optically transparent draft shield assembly 32.

Heat from overhead infrared heater 14 is radiated to an infant placed on mattress assembly 22 through optically transparent draft shield assembly 32 when the draft shield is in either the completely closed position or in the partially open position. As described below, optically transparent draft shield assembly 32 is so arranged that it can remain in position over an infant on mattress assembly 22 when side panels 26, 28 and 30 are in their open positions.

Figure 5:
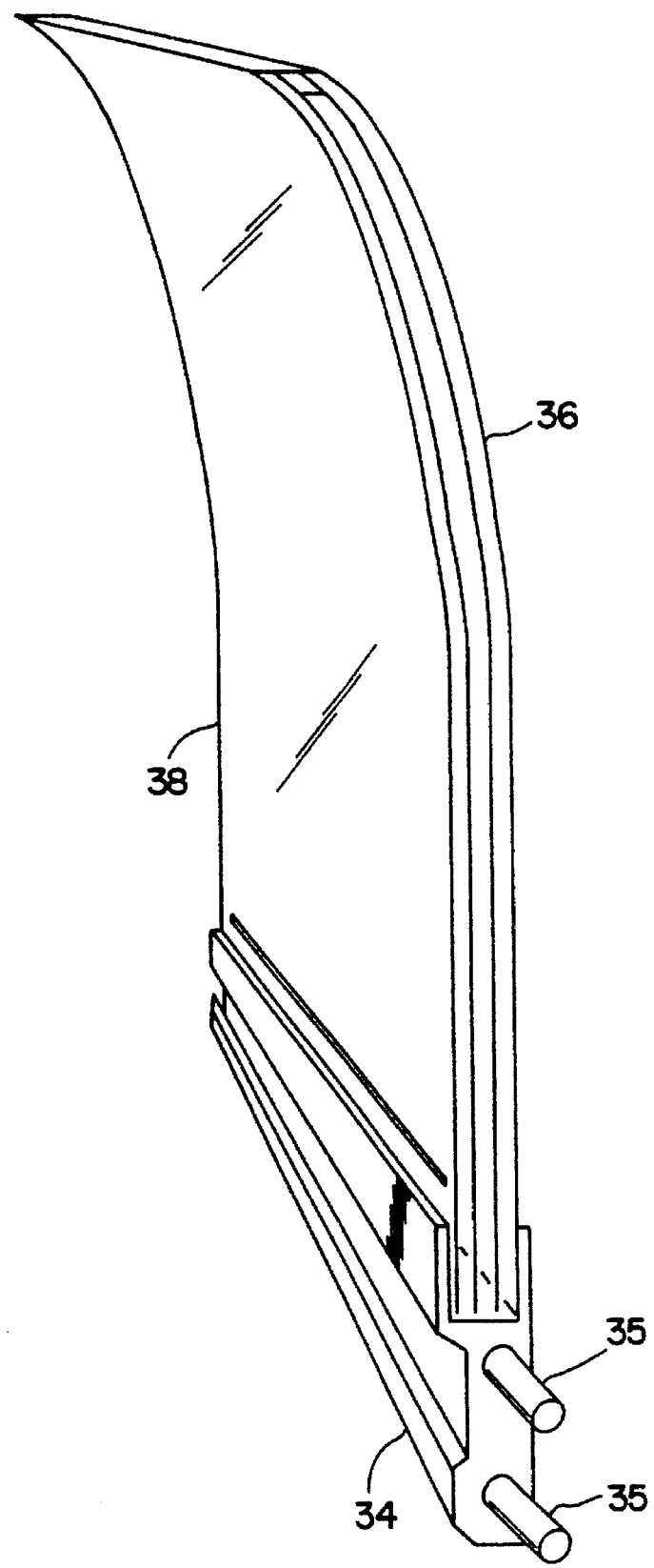
FIG. 5 is a perspective sectional view, similar to FIG. 2B, of a second preferred embodiment of an optically transparent electrothermal side panel included in an infant radiant warmer constructed in accordance with the present invention.

As shown in FIG. 4, vertically disposed optically transparent electrothermal side panels 24, 26, 28 and 30 are disposed in a rectilinear array with side panel 24 at a head end, side panel 26 at a foot end opposite from the head end, and side panels 28 and 30 extending between side panels 24 and 26. Each of the vertically disposed optically transparent electrothermal side panels 28 and 30 preferably is curved, as shown in FIG. 5, to focus heat radiated from these side panels to the infant.

Figure 2A:
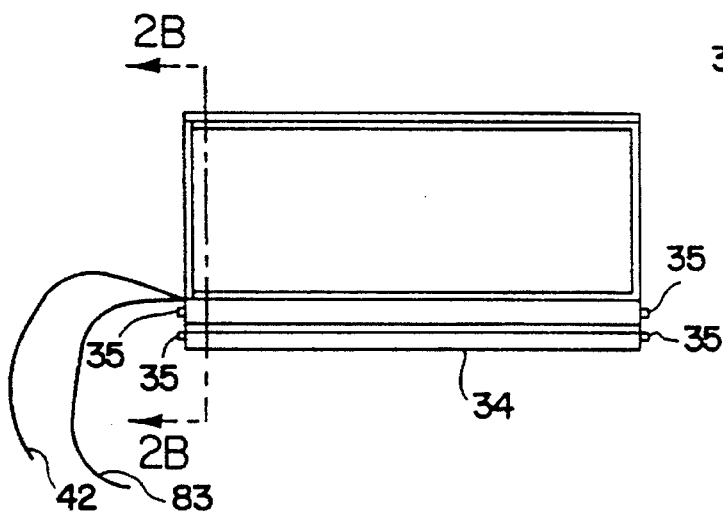
FIG. 2A is a front view of a first preferred embodiment of an optically transparent electrothermal side panel included in an infant radiant warmer constructed in accordance with the present invention.
Figure 2B:
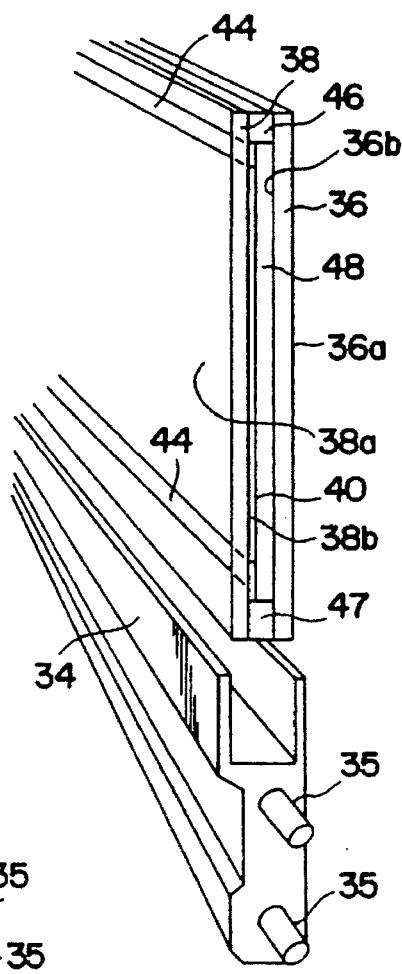
FIG. 2B is a perspective sectional view of the optically transparent electrothermal side panel of FIG. 2A taken along line 2B—2B of FIG. 2A.

As already mentioned, vertically disposed optically transparent electrothermal side panels 26, 28 and 30 preferably are hinged to the base 33 of bassinet assembly 12 for pivotal movement of these side panels to permit access to the infant without moving optically transparent draft shield assembly 32 from its completely closed position. As shown in FIGS. 2A and 2B, vertically disposed optically transparent electrothermal side panels 26, 28 and 30 each fit in a side panel extrusion 34 which has a pair of studs 35 at each end. Studs 35 fit into associated slots in posts (not shown) at the corners of base 33 of bassinet assembly 12. By lifting the side panel vertically, so that studs 35 move vertically in their associated slots to a position at which the side panel can swing outwardly, side panels 26, 28 and 30 can be moved to an open position represented by the dashed lines identified by reference numeral 26b in FIG. 1 for side panel 26.

As shown most clearly in FIGS. 2A and 2B, for the embodiment of the invention being described, each of the vertically disposed optically transparent electrothermal side panels 24, 26, 28, and 30 includes a pair of spaced apart outer and inner sheets 36 and 38, respectively. These sheets can be formed of a suitable transparent acrylic. Outer sheet 36 has a first surface 36a facing the atmosphere outside bassinet assembly 12 and a second surface 36b facing the space between sheets 36 and 38. Inner sheet 38 has a first surface 38a facing the atmosphere within bassinet assembly 12 and a second surface 38b facing the space between sheets 36 and 38.

Each of the vertically disposed optically transparent electrothermal side panels 24, 26, 28, and 30 also includes a transparent conductive film 40 coated on surface 38b of inner sheet 38. Transparent conductive film 40 can be, for example, an indium tin oxide layer on a PET layer with the transparent conductive film applied to surface 38b of inner sheet 38 by a suitable adhesive. When transparent conductive film 40 is electrically powered by means of a line cord 42, shown in FIG. 2A, and buss strips 44, shown in FIGS. 2B, the side panel serves both as a radiant shield which reduces radiant heat losses from the infant and a source of radiant heat which adds to the warmth provided by overhead infrared heater 14 to the infant. U.S. Pat. No. 5,119,467 discloses the construction and operation of transparent heater panels and is incorporated herein by reference.

A top closure member 46, a bottom closure member 47, and two end closure members 48, only one of which is shown in FIG. 2B, serve to seal the space between outer sheet 36 and inner sheet 38. This space is sealed against humidity and contaminants.

As shown most clearly in FIG. 4, for the embodiment of the invention being described, optically transparent draft shield assembly 32 preferably is an articulated unit which includes first and second cover frames 50 and 52 attached to one another by a pair of hinges 53 for pivotal movement of cover frame 52 upward and backward over cover frame 50. Optically transparent draft shield assembly 32 also includes a PVC film supply roll 54 on a roll core rod 56 which fits into a pair of slots 58 in a supply roll cradle 60 which, in turn, fits over and is mounted to optically transparent electrothermal side panel 24 by means of a mount member 61. Cover frame 50 is attached to mount member 61 by a piano hinge 62 for pivotal movement of cover frame 50 relative to mount member 61. With this construction, cover frame 52 can be folded back over cover frame 50 to the partially open position of optically transparent draft shield assembly 32 identified by reference numeral 32b in FIG. 1 and cover frame 50 can be folded back toward post 16 of base 10 to the completely open position of the draft shield assembly identified by reference numeral 32a in FIG. 1. In the completely open position of optically transparent draft shield assembly 12, the leading edge of cover frame 52 can be fitted into slots 58 in supply roll cradle 60 to secure the draft shield assembly in its completely open position. A pair of gussets 63, one attached to the underside of each of the lateral sides of cover frame 50 and movable with cover frame 50, bear against mount member 61 when draft shield assembly 32 is in the closed position shown in FIG. 4 to provide cantilever support even when side panels 26, 28 and 30 are in their open positions.

Lengths of the PVC film can be rolled off supply roll 54 onto cover frame 50 and 52. Used lengths of the PVC film are torn off along perforation lines 64 and disposed of. The PVC film is held secure on cover frames 50 and 52 by suitable means such a high tack tape 65 extending along the edges of the PVC film which adheres to a TFE tape 66, extending along the lateral edges of cover frames 50 and 52, after a removable tack strip 67 has been removed from the high tack tape.

Figure 6:
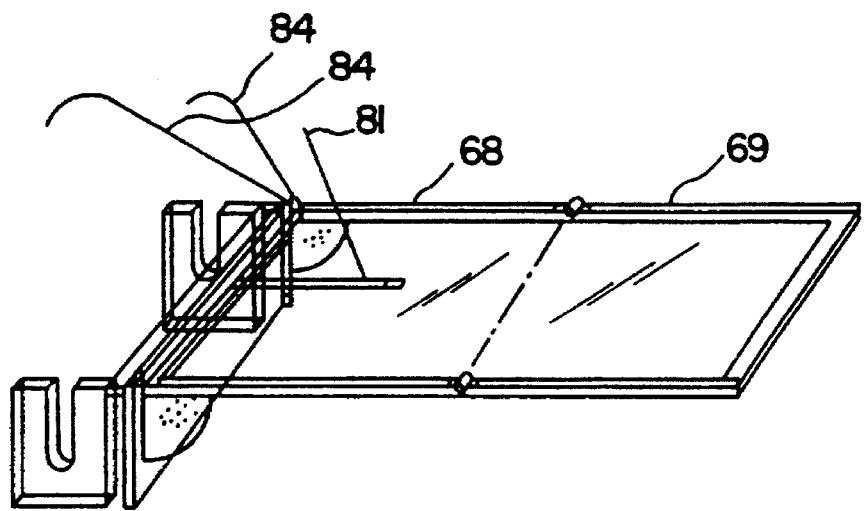
FIG. 6 is a perspective view of a second preferred embodiment of a draft shield assembly constructed in accordance with the present invention and included in an infant radiant warmer constructed in accordance with the present invention.
Figure 6A:
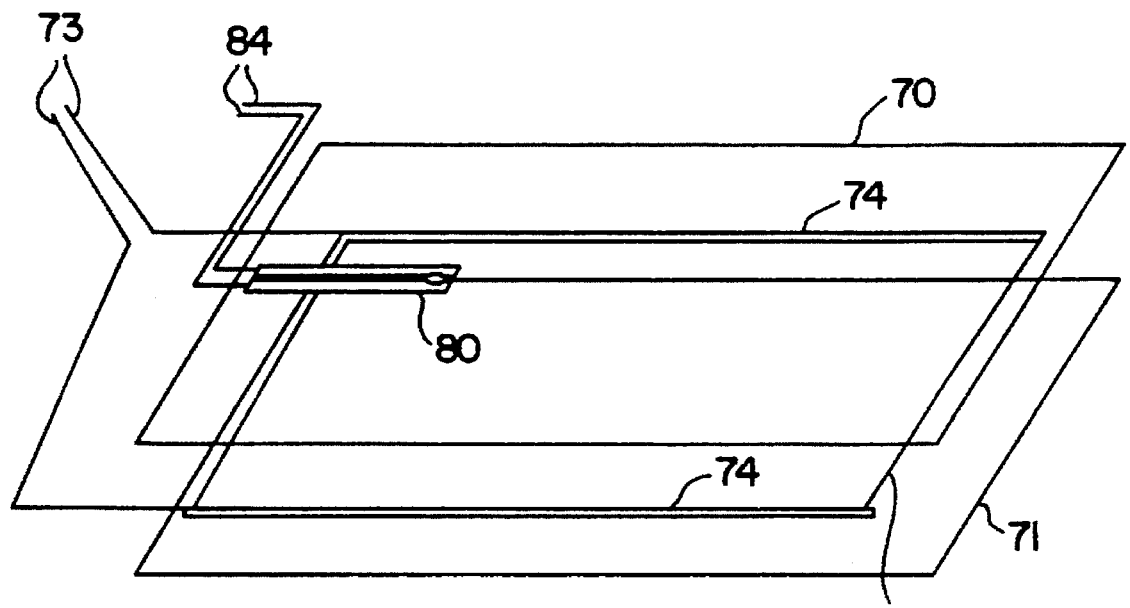
FIG. 6A is an exploded perspective view of a portion of the draft shield assembly of FIG. 6.

In an alternative construction of the optically transparent draft shield assembly, the cover members can be optically transparent electrothermal panels generally similar in construction to optically transparent electrothermal side panels 24, 26, 28, and 30. Specifically, as shown in FIGS. 6 and 6A, cover members 68 and 69 each include upper and lower protective sheets 70 and 71 with a transparent conductive film 72 sandwiched between the two protective sheets which is powered by a line cord 73 and buss strips 74. When so arranged, cover members 68 and 69 serve a three-fold purpose. First, they serve as a draft shield in the same manner as the first draft shield assembly described above. Second, they serve as a radiant shield which reduces radiant heat losses from the infant. Third, they serve as a source of radiant heat and provide warmth to the infant when overhead infrared heater 14 is not in operation or add to the warmth provided by the overhead infrared heater to the infant when the overhead infrared heater is in operation.

An infant radiant warmer, constructed in accordance with the present invention, preferably includes a control switch 75 mounted on vertical post 16 of base 10 which is engaged by optically transparent draft shield assembly 32 when the draft shield assembly is completely opened. Control switch 75, when engaged by optically transparent draft shield assembly 32, serves to actuate overhead infrared heater 14 to provide radiated heat from the overhead infrared heater when the draft shield assembly is open and the interior of bassinet assembly 12 is exposed to the atmosphere outside the bassinet assembly.

Figure 3:
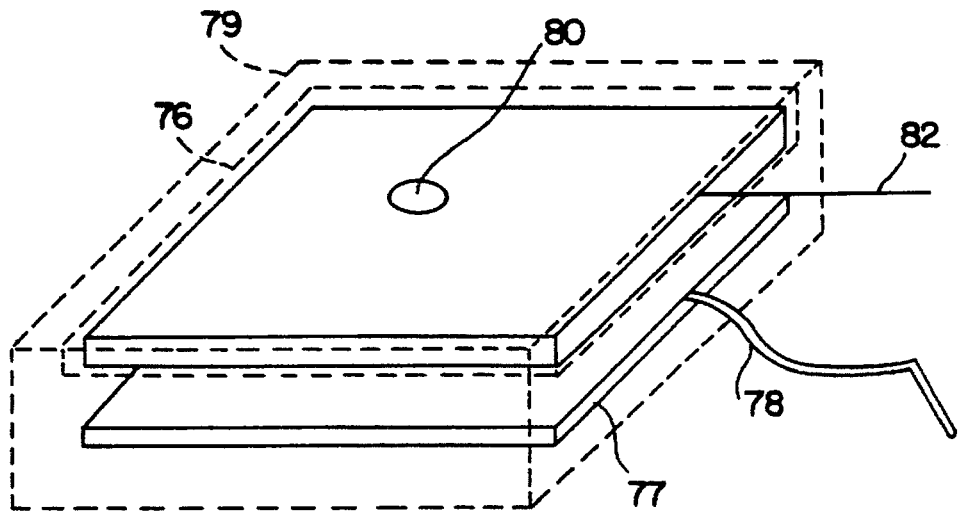
FIG. 3 is a perspective view of a preferred embodiment of a mattress assembly included in an infant radiant warmer constructed in accordance with the present invention.

FIG. 3 illustrates a preferred form of a mattress assembly for inclusion in an infant radiant warmer constructed in accordance with the present invention. This mattress assembly includes a mattress 76 and a heater panel 77 positioned beneath the mattress which is powered by a line cord 78. Mattress 76 and heater panel 77 are contained within an outer cover 79. Heater panel 77 has a transparent conductive film coated on a rigid base which can support mattress 76 and an infant on the mattress. Preferably, mattress 76 is an air mattress or formed from a material which absorbs a minimum amount of heat, so that heat radiated from heater panel 77 is conducted to an infant on mattress 76. The entire mattress assembly preferably is X-ray transparent, so that an X-ray cassette can be positioned beneath the mattress assembly when X-ray images are to be taken of an infant on the mattress assembly.

An infant radiant warmer, constructed in accordance with the present invention, also includes means for controlling the power supplied to overhead infrared heater 14, to optically transparent electrothermal side panels 24, 26, 28, and 30, to mattress assembly 22, and to optically transparent draft shield assembly 32 when the cover members are arranged as sources of radiant heat as illustrated in FIGS. 6 and 6A. Such means, which can be of conventional construction and operation, include sensors, for example the surface thermal probe 80 included in mattress assembly 22 shown in FIG. 3 and the sensor 81 included in cover member 68 shown in FIGS. 6 and 6A, which sense the temperature of the component or region of interest and develop a signal representative of the sensed temperature. This signal is conducted, for example, by the thermal probe conductor 82 also included in mattress assembly 22 shown in FIG. 3, the thermal probe conductor 83 included in the optically transparent electrothermal side panels 24, 26, 28 and 30 shown in FIG. 2A and the sensor lead wires 84 included in the optically transparent electrothermal draft shield assembly shown in FIGS. 6 and 6A, to suitable electronic circuitry (not shown) for regulating the power delivered to the particular component which affects the temperature being sensed to control this component in response to the temperature which is sensed and a set point temperature established by personnel attending to the infant under treatment. For example, if a sensor of an optically transparent electrothermal side panel indicates a temperature corresponding to the region of the infant closest to this side panel below the system set point temperature, that side panel will be controlled to respond by providing heat to raise the temperature of the measured region.

Figure 7A:
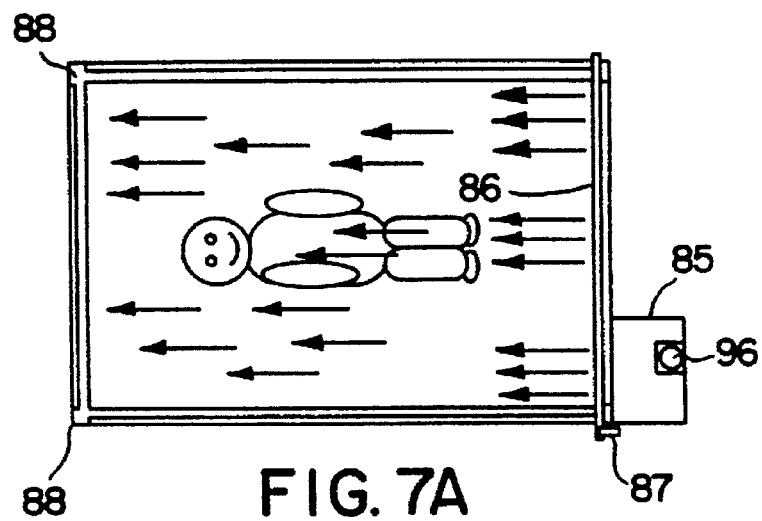
FIG. 7A is a top view of a preferred embodiment of humidifying apparatus constructed in accordance with the present invention and which can be included in an infant radiant warmer constructed in accordance with the present invention.

An infant radiant warmer, constructed in accordance with the present invention, preferably includes means for humidifying the atmosphere within bassinet assembly 12 in which an infant is placed. As shown in FIG. 7A, such means include, for the embodiment of the invention being described, a humidifier 85 and a humidity diffuser 86 through which humidified gas, either air or oxygen, is introduced into the atmosphere within bassinet assembly 12 in which an infant is placed. The humidified gas is supplied from humidifier 85 to humidity diffuser 86 through a connecting tube 87.

The arrows in FIG. 7A indicate the direction of flow of humidified gas when humidity diffuser 86 is located only at the head end of bassinet assembly 12. The humidified gas exits bassinet assembly 12 at the open corners 88 at the foot end of the bassinet assembly. Depending on the design of bassinet assembly 12, the humidity diffuser can be arranged to extend along the sides of the bassinet assembly as well as along the head end of the bassinet assembly.

Figure 7B:
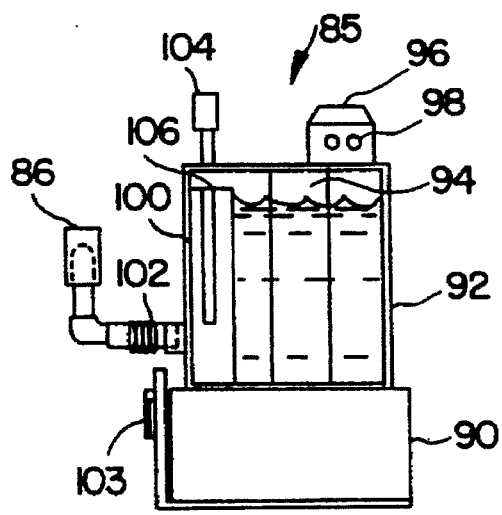
FIG. 7B is a side view of the humidifier portion of the FIG. 7A humidifying apparatus.

Referring to FIG. 7B, humidifier 85 includes a base 90 which contains the humidifier electronics and controls and a water reservoir 92 which rests on base 90 but is removable from base 90 for filling and cleaning. A heater tower 94, mounted to base 90, extends through water reservoir 92 when the water reservoir rests on base 90 and heats water in the water reservoir. Water reservoir 92 is filled with water through a fill port at the top of the water reservoir.

Air to be humidified is drawn through a filter 96 into humidifier 85 by a fan 98. As the filtered air passes over the heated water in water reservoir 92, it is humidified and the humidified air exits humidifier 85 through a vertical standpipe 100 which has an opening at its top which is above the water line of the water in the water reservoir. Humidified air is conducted from humidifier 85 to humidity diffuser 86 through an outlet coupling 102. Humidifier 85 has a suitable mounting bracket 103 by means of which the humidifier can be mounted to bassinet assembly 12.

Humidifier 85 also has a coupling 104 adapted for connection to a source of pressurized oxygen. Oxygen passes through a venturi tube 106 and mixes with the humidified atmosphere at the bottom of standpipe 100. Humidified oxygen is conducted from humidifier 85 to humidity diffuser 86 through outlet coupling 102.

Figure 7C:
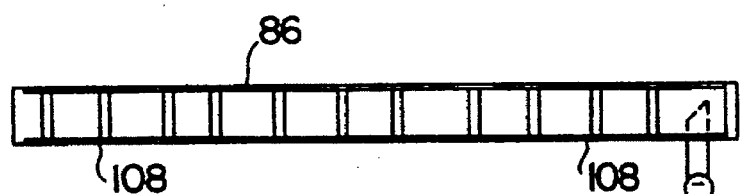
FIG. 7C is a front view of the humidity diffuser portion of the FIG. 7A humidifying apparatus.
Figure 7D:
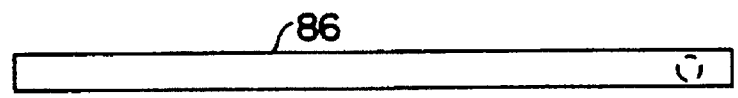
FIG. 7D is a top view of the humidity diffuser portion of the FIG. 7A humidifying apparatus.

Referring to FIGS. 7C and 7D, humidity diffuser 86 is an elongated tube of rectangular cross-section with its ends closed. The humidity diffuser has a plurality of openings 108 in one of its faces through which humidified gas, either air or oxygen, enters the atmosphere within bassinet assembly 12 in which an infant is placed.

While in the foregoing there have been described preferred embodiments of the present invention, it should be understood by those skilled in the art that various modifications and changes can be made without departing from the true spirit and scope of the present invention.

What is claimed:

1. A draft shield comprising:
   first and second cover frames hinged together for pivotal movement of said first cover frame relative to said second cover frame;
   means adapted for attaching said second cover frame to a base for pivotal movement of said second cover frame relative to said base;
   a supply of thin-film transparent plastic material mounted to said attaching means;

means for drawing selected lengths of said thin-film transparent plastic material from said supply; and means for securing said selected lengths of said thin-film transparent plastic material drawn from said supply to said first and said second cover frames.

2. A draft shield comprising:

first and second cover members hinged together for pivotal movement of said first cover member relative to said second cover member, each of said cover members including upper and lower protective sheets and a transparent conductive film sandwiched between said upper and said lower protective sheets;

means adapted for attaching said second cover member to a base for pivotal movement of said second cover member relative to said base; and means for conducting electrical power to said transparent conductive films.

* * * * *